United States Patent [19]

Bycroft et al.

[11] Patent Number: 5,593,827
[45] Date of Patent: Jan. 14, 1997

[54] AUTOINDUCER

[75] Inventors: Barrie W. Bycroft; Paul Williams, both of Nottingham; Gordon S. A. B. Stewart; Siri R. Chhabra, both of Loughborough; Paul Stead, Broadstone; Michael K. Winson, Nottingham; Philip J. Hill, Nottingham; Catherine E. D. Rees, Nottingham; Nigel J. Bainton, Nottingham, all of United Kingdom

[73] Assignee: The University of Nottingham, Nottingham, United Kingdom

[21] Appl. No.: 137,036

[22] PCT Filed: Apr. 16, 1992

[86] PCT No.: PCT/GB92/00713

§ 371 Date: Oct. 18, 1993

§ 102(e) Date: Oct. 18, 1993

[87] PCT Pub. No.: WO92/18614

PCT Pub. Date: Oct. 29, 1992

[30] Foreign Application Priority Data

Apr. 18, 1991 [GB] United Kingdom .................. 9108307

[51] Int. Cl.$^6$ ...................................................... C12Q 1/68
[52] U.S. Cl. ................... 435/6; 435/34; 540/202; 548/124; 549/321; 549/322
[58] Field of Search .................... 435/6, 7.2, 8, 69.1, 435/172.3, 244, 252.1, 34; 540/202, 364, 451, 454, 460, 463, 462, 470, 482, 483; 548/124; 549/321, 322

[56] References Cited

U.S. PATENT DOCUMENTS

| | | | |
|---|---|---|---|
| 4,861,709 | 8/1989 | Ulitzur et al. | 435/6 |
| 5,196,318 | 3/1993 | Baldwin et al. | 435/69.1 |

OTHER PUBLICATIONS

Devine et al., "Proc. Natl. Acad. Sci. USA", 86 5688–5692 (Aug. 1989) Biochemistry Identification of the Operator of the lux regulon from the *Vibrio fischeri* Strain ATCC7744.

Eberhard et al., "Arch. Microbiol." 146 35–40 (1986), Analogs of the Autoinducer of Bioluminescence in *Vibrio fischeri*.

Eberhard et al., "Biochemistry", 20 2444–2449 (1981) Structural Identification of Autoinducer of *Photobacterium fischeri* Luciferase.

Greenberg et al., "Arch. Microbiol.", 120 87–91 (1979), Induction of Luciferase Synthesis in *Beneckea harveyi* by Other Marine Bacteria.

Jie–Gang Cao et al., The Journal of Biological Chemistry, pp. 21670–21676 (1989) vol. 246(136).

Mar. (1968) "Advanced Organic Chemistry: Reactions, Mechanisms, and Structure", pp. 71–75, 92–94, McGraw–Hill, N.Y.

Meighen (1991) Microbl. Rev. 55(1), 123–142.

*Primary Examiner*—James S. Ketter
*Attorney, Agent, or Firm*—Wenderoth, Lind & Ponack

[57] ABSTRACT

The compound N-(β-ketocaproyl)L-homoserine lactone is shown to be an autoinducer that enhances gene expression in a wide variety of microorganisms. Use can be made of this property for diagnostic purposes, e.g., when gene expression causes bioluminescence or antibiotic production, or to promote bacterial growth. The invention claims use for these purposes of the compound and analogs of formula (I) where n is 2 or 3, each of X and Y is O, S or NH, and R is optionally-substituted C1–C12 alkyl or acyl. Some of these are also claimed as new compounds.

21 Claims, 3 Drawing Sheets

FIG. 2  N-(B-ketocaproyl)-homoserine lactone  Vibrio fischeri autoinducer
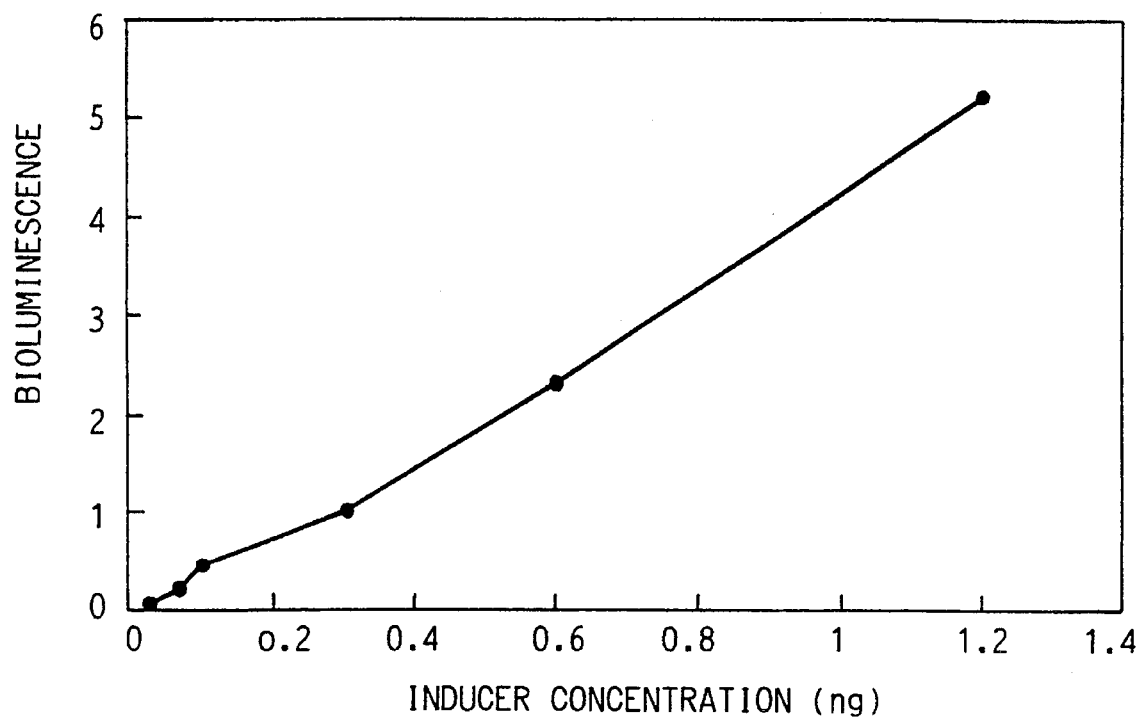
Light from E.coli(pSB237) after 24 h incubation with autoinducer
FIG. 3
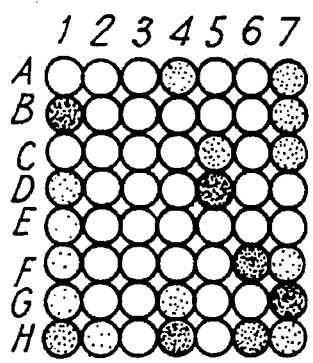
AFTER 6 HOURS OF INCUBATION
FIG. 5
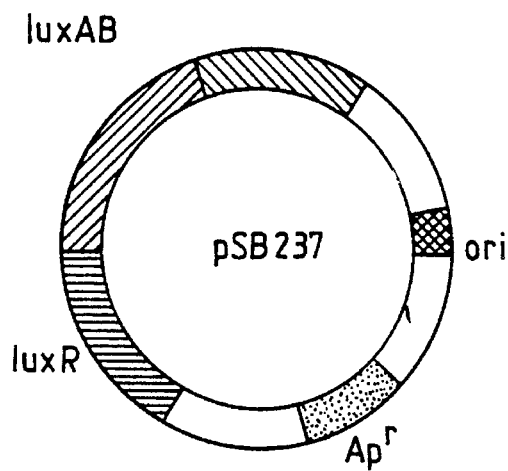

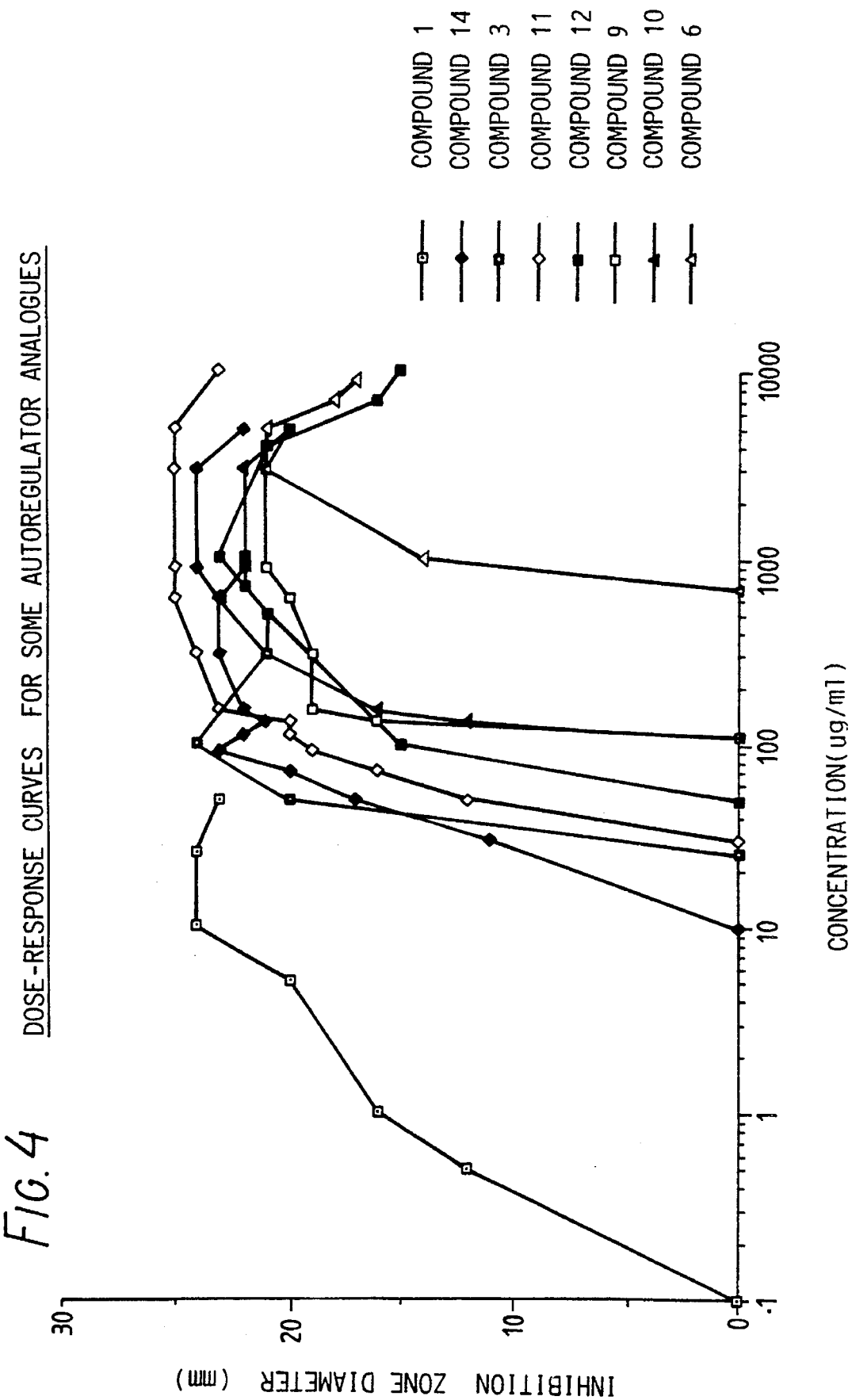

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 45 base pairs
        ( B ) TYPE: Nucleic acid
        ( C ) STRANDEDNESS: Single
        ( D ) TOPOLOGY: Linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:
        ( B ) STRAIN:
        ( C ) INDIVIDUAL ISOLATE:
        ( D ) DEVELOPMENTAL STAGE:
        ( E ) HAPLOTYPE:
        ( F ) TISSUE TYPE:
        ( G ) CELL TYPE:
        ( H ) CELL LINE:
        ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY:
        ( B ) LOCATION:
        ( C ) IDENTIFICATION METHOD:
        ( D ) OTHER INFORMATION:

( x ) PUBLICATION INFORMATION:

( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:1:

AAGCTTGAAT TCCCGGGTTA ATTTTTAAAG TATGGGCAAT CAATT                45

( 2 ) INFORMATION FOR SEQ ID NO:2:

( i ) SEQUENCE CHARACTERISTICS:
            ( A ) LENGTH: 43 base pairs
            ( B ) TYPE: Nucleic acid
            ( C ) STRANDEDNESS: Single
            ( D ) TOPOLOGY: Linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

( v i i i ) POSITION IN GENOME:
            ( A ) CHROMOSOME/SEGMENT:
            ( B ) MAP POSITION:
            ( C ) UNITS:

( i x ) FEATURE:
            ( A ) NAME/KEY:
            ( B ) LOCATION:
            ( C ) IDENTIFICATION METHOD:
            ( D ) OTHER INFORMATION:

( x ) PUBLICATION INFORMATION:
            ( A ) AUTHORS:
            ( B ) TITLE:
            ( C ) JOURNAL:
            ( D ) VOLUME:
            ( E ) ISSUE:
            ( F ) PAGES:
            ( G ) DATE:
            ( H ) DOCUMENT NUMBER:
            ( I ) FILING DATE:
            ( J ) PUBLICATION DATE:
            ( K ) RELEVANT RESIDUES IN SEQ ID NO:

( x i ) SEQUENCE DESCRIPTION: SEQ ID NO:2:

TTTTATGAAT TCTACGTAAC CAACCTCCCT TGCGTTTATT CGA                43

AUTOINDUCER

An autoinducer is a chemical molecule, often quite a small one, which is produced by a microorganism during metabolism and which then acts to increase the expression of genes of the microorganism.

N-(β-ketocaproyl) homoserine lactone [3-oxo-N-(tetrahydro-2-oxo-3-furanyl)hexanamide (formula 2) has long been recognised as an autoinducer regulating expression of lux genes and hence the bioluminescent phenotype in the marine microorganism, *Vibrio fischeri* (Eberhard et al., 1981). Although characterised as a bacterial pheromone (Eberhard, 1972), it has been identified only in the one species of bioluminescent bacteria and any broader role in signalling, such as communicating nutritional viability to other bacteria (Eberhard et al., 1981) has previously had no foundation in scientific evidence. It has been observed that the autoinducer of *Vibrio fischeri* is similar in structure to A-factor (formula 4), a regulatory molecule which is produced by *Streptomyces griseus* (Silverman et al., 1989; Meighen, 1991) and which causes a self-induction of sporulation and streptomycin synthesis. Intellectually, this has been assimilated by several workers as suggestive of a broader role for such molecules. To establish precisely the current level of understanding, we quote from two recent reviewers:

"Perhaps this chemical relationship is an indication that mechanisms used by bacteria to sense their environments have a common origin and that there is a large class of signalling molecules or bacterial hormones similar in structure and mode of action." (Silverman et al., 1989).

"The possibility that the lux autoinducers are part of a larger class of signalling molecules (allomones, pheromones or hormones) used to sense the local nutritional or chemical environment has been suggested." (Meighen, 1991).

While these two statements establish the possibility of a large class of signalling molecules, it must be re-emphasised that there is no basis in experimentation for confirming the above hypothesis and certainly no indication that N-(β-ketocaproyl) homoserine lactone (formula 2) may be directly involved in gene regulation of microorganisms other than *Vibrio fischeri* and the closely related *Vibrio logei*. In addition, a study of other bacteria, including nonluminous species, for their ability to provide autoinducer for the related *Vibrio harveyi* system (N-β-hydroxybutyryl homoserine lactone) (formula 3) failed to identify any terrestrial sources for complementation (Greenberg et al., 1979).

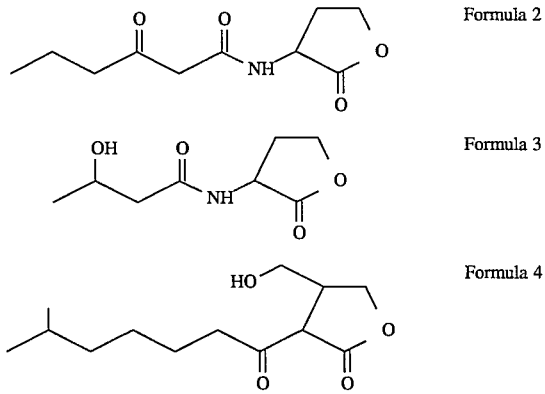

Formula 2

Formula 3

Formula 4

In a research programme directed at the study of carbapenem synthesis in prokaryotes, we have recently discovered that the compound of formula 2 regulates the expression of carbapenem synthesis in Erwina. It appears that there is a family of compounds, including those of formulae 2 and 3 and analogues thereof, which control (increase or decrease) gene expression in a variety of microorganisms. This family is sometimes hereinafter referred to as "N-(β-ketocaproyl) homoserine lactone or analogue". Some of this family of compounds, including specifically those of formulae 2 and 3, are produced by various microorganisms for which they act as autoinducers.

BRIEF SUMMARY OF THE INVENTION

We have synthesised various members of this family of compounds, including optically active isomers thereof. This invention includes as new compounds those members of the family that have not been previously described. The invention also includes use of the compounds of the family to control gene expression in microorganisms. Some of the practical implications of this use are discussed below.

Thus in one aspect the invention provides use of a compound having the formula 1 to control gene expression in microorganisms other than *V. fischeri*, *V. logei* and *V. harveyi*, wherein formula 1 is

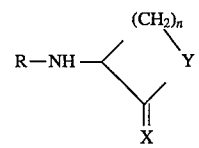

where
n is 2 or 3
Y is O, S or NH
X is O, S or NH
R is $C_1$–$C_{12}$ alkyl or acyl which may be substituted.

Preferably n is 2, so that the ring is five-membered. Although it is not necessary for Y and X to be the same, both are preferably O as in the compounds of formulae 2 and 3. Preferably R is C2 to C6 acyl. Preferably R carries a keto or hydroxy group in the β position.

In another aspect, the invention provides, as new compounds, optically active isomers of the compounds of formula 1 as defined above. Preferably the optically active isomers are L-isomers, since these have proved more active than their corresponding D-isomers at increasing gene expression. The D-isomers may be useful to inhibit gene expression.

Use is made of these compounds to control gene expression in microorganisms. The control exercised may be to decrease, but is more usually to increase, gene expression. The microorganisms concerned include bacteria, both Gram negative and Gram positive, yeasts and fungi. It is at the basis of the invention that a wide variety of microorganisms have some gene whose expression is affected in some way by at least one compound within the family. This control technique often involves the use of microorganisms that are not themselves capable of producing an autoinducer within the family of compounds, but which are capable, in the presence of exogenous autoinducer, of expressing a gene, generally in an easily detectable manner. Two examples of such microorganisms, which are discussed in more detail below, are:

- A genetic construct pSB237. This has the capacity to express a bioluminescent phenotype in *E. coli*, but only in the presence of added inducer, preferably the compound of formula 2.
- A mutant strain B10002/mu22, made by mutation of *Erwinia carotovora* carotovora ATCC3948. Unlike its parent, the mutant 22 is capable of synthesising carbapenem antibiotic only in the presence of added inducer, such as the compound of formula 2.

In one example of such technique, the invention provides a method of testing for N-(β-ketocaproyl) homoserine lactone or analogue in a sample, by incubating the sample in contact with test bacteria chosen for enhancement of gene expression by the lactone or analogue, and detecting the gene expression as a test for the lactone. The limits of detection using a bioluminescent phenotype derived from *E. coli* [pSB237] depend upon the time of exposure of the bacterial culture to inducer. As shown in Example 4 below, at concentrations above 10 ng/ml of culture, induction of bioluminescence takes less than 10 minutes. At lower concentrations induction is progressively slower, but concentrations of as low as 80 pg/ml can be distinguished from a zero concentration control after some 20 hours of incubation.

In another example of this technique, the invention provides a method of testing for the presence in a sample of a first bacterium known to generate N-(β-ketocaproyl) homoserine lactone or analogue under particular conditions, which method comprises incubating the sample under the particular conditions in contact with a test bacterium chosen for enhancement of gene expression by the lactone or analogue, and detecting the gene expression as a test for the first bacterium.

Such a test may be for bacteria generally, or for specific bacteria known to produce autoinducer under particular conditions. For example, *Pseudomonas aeruginosa* produces autoinducer (formula 2) only under defined growth conditions (see Example 4), specifically the use of limiting or minimal growth media supplemented with Fe(III). Similarly, there is preliminary evidence that *Listeria monocytogenes* produces a lactone or analogue only after exposure to low temperature. These characteristics of particular bacteria provide the basis of specific tests for those bacteria in a mixture of microorganisms.

*P. aeruginosa* is a bacterium that must be stipulated as absent in 100 ml of $H_2O$ to be used for the preparation of pharmaceutical products, particularly injectables. There is therefore a considerable need to develop a rapid assay system for this specific bacterium. Existing rapid assays such as DNA probes or antibody probes cannot discriminate between live and dead cells, an unacceptable limitation only avoidable by testing after microbial growth. Novel processes such as the construction of genetically engineered bacteriophage specific for *P. aeruginosa* and containing the luxAB genes are a possibility but cost of development is high.

The fact that *P. aeruginosa* produces a substance capable of complementing inducer in a luxR/AB construct provides the basis of a rapid test.

It has been demonstrated that the normal density dependent expression of the entire lux operon in *E. coli* can be suppressed. In liquid growth a lux operon construct would not emit high levels of light until the culture density approached the end of exponential growth. If, however, such cells are immobilised in a low concentration gel the bacteria will light up very rapidly. It is presumed that this is a consequence of limiting the diffusion of the autoinducer.

A concept assay for *P. aeruginosa* may be as follows. Water is filtered to collect any bacteria and the filter overlayed with a gel (agar, agarose or gelatin) containing *E. coli* [pSB237]. The inducer produced by live *P. aeruginosa* cells is limited in diffusion and rapidly reaches a concentration sufficient to activate bioluminescence in the surrounding *E. coli* cells. In effect light plaques appear and can be detected and counted. The ability to control the optimal media conditions for production of complementing activity allows for considerable specificity of the assay.

In yet another example of the technique, a compound according to formula 1 can be added to a microorganism culture in order to cause expression of a particular gene that would not otherwise be expressed. For example, the compound may be used to induce antibiotic production.

In yet another example, growth media for microorganisms e.g. bacteria can be prepared containing an autoinducer—at an effective concentration which would lead to a stimulation or promotion of the metabolism, growth and/or recovery of the organisms. (These phenomena are herein referred to collectively as growth.). This may include all the organisms present or, in some cases, it may enhance a selected group of organisms in a sample in preference to the others.

BRIEF DESCRIPTION OF THE DRAWINGS

FIG. 2 is a graph depicting bioluminescence variations versus inducer concentration (ng), for N-(β-ketocaproyl)-homoserine lactone *Vibrio fischeri* autoinducer, measuring bioluminescence emitted from *E. coli* (pSB237) after twenty-four hours incubation with said autoinducer.

FIG. 3 depicts a table of microorganisms which provide complementation for activation of bioluminescence with *E. coli* (pSB237).

FIG. 4 is a graph depicting dose-response curves for some autoregulator analogs, with respect to inhibition zone diameter (mm) vs. concentration.

FIG. 5 is a plasmid map for *E. coli* (pSB237).

Figure 1:
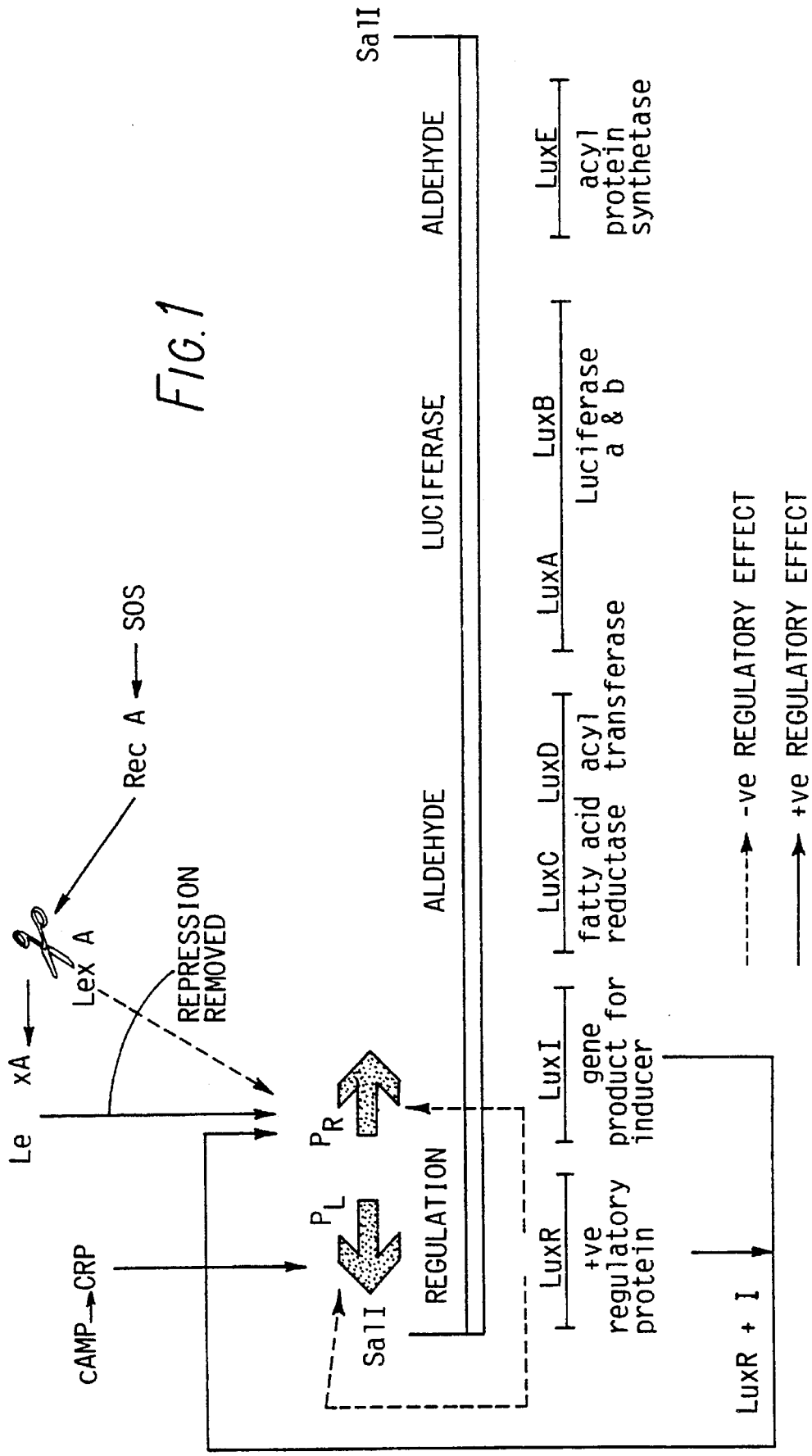
FIG. 1 is a flow sheet describing the regulation of the lux operon of *Vibrio fischeri*.

A lot of work has been done on the regulation of the lux operon of *Vibrio fischeri*, in which the autoinducer of formula 2 plays a crucial role. Reference is directed to FIG. 1 of the accompanying drawings. The following paragraphs describe the current state of knowledge regarding the role of autoinducer in the control of the lux operon and should be read in conjunction with FIG. 1.

The phenomenon of autoinduction was first described by Nealson et al. (1970), based on observations that *Vibrio harveyi* and *Vibrio fischeri* produce light only at high cell densities, and that these bacteria produce a substance which will induce bioluminescence in cultures of low cell density. It was postulated that a substance termed autoinducer accumulates in the growth media and induces the synthesis of the components of the bioluminescence system (when its concentration reaches 1–2 molecules per bacterial cell). Therefore, it is not cell density per se which influences bioluminescence, but the accumulation of the autoinducer molecule. The first autoinducer molecule to be purified and structurally identified was that produced by *Vibrio fischeri*, and was found to be N-(β-ketocaproyl)homoserine lactone (Eberhard et al., 1981). It was speculated that as this molecule combines homoserine lactone, an intermediate in amino acid metabolism and β-ketocaproic acid, a relative of fatty acid metabolism intermediates, that it could be a signal of nutritional viability communicated to other bacteria perhaps to induce a chemotactic response, hence the autoinducer became considered a bacterial pheromone (Eberhard, 1972) with a role in population sensing.

The luxI gene which lies upstream of luxC in *V. fischeri* codes for a 22 kD polypeptide believed to be responsible for production of autoinducer, apparently from cytoplasmic precursors (Engebrecht et al., 1983) although exactly what these precursors are is not clear. There is no evidence that any systematic search for genes analogous to luxI in other luminous bacteria has been attempted.

In 1987 Kaplan and Greenberg identified a positive regulatory element in *V. fischeri* which was required along with autoinducer to activate transcription of the structural genes for bioluminescence (luxCDABE) and for autoinducer synthesis (luxI product). This regulatory protein was found to be a 28 kD polypeptide coded for by luxR, a gene which lies upstream of luxI but which is transcribed in the opposite direction to the other lux genes. The luxR product was shown to be a DNA-binding protein, although under the conditions used the binding was not lux DNA-specific. The reason suggested for this was incorrect renaturation of the protein during purification, an explanation further supported by problems of reproducibility when trying to demonstrate binding of autoinducer. Mutational analysis of luxR has indicated that one region, near the centre of the luxR polypeptide, constitutes an autoinducer binding domain, while a region towards the carboxy terminus of the polypeptide constitutes a lux operator DNA binding/recognition domain (Slock et al., 1990). The position of the autoinducer binding site has subsequently been localised between amino acid residues 79–127 of the *V. fischeri* luxR protein (Shadel et al., 1990). This could, therefore represent a highly conserved region within luxR homologs.

More recently, a region unlinked to the lux structural genes has been identified as a locus controlling bioluminescence in *V. harveyi*, which, unlike *V. fischeri*, does not possess lux regulatory genes as part of an integral operon required for bioluminescence (Martin et al., 1989). Nevertheless, there is a region upstream of luxC in *V. harveyi* that contains a strong inducable promoter, which is cell density regulated and glucose repressible (Miyamoto et al., 1990). The unlinked regulatory locus from *V. harveyi* (named luxR) has been cloned and sequenced (Showalter et al., 1990), and the results indicate a structural relationship to some DNA binding proteins (i.e. the DNA-binding domain of Cro-like proteins). There is, however, no sequence similarity to the luxR gene of *V. fischeri*. Furthermore, the cloned luxR from *V. harveyi* is unresponsive to exogenously supplied autoinducer and does not direct the synthesis of an autoinducer activity. The cloning of this regulatory locus into *E. coli* together with luxCDABE does not reconstruct a lux regulatory system reflective of *V. harveyi*. It has been suggested, therefore, that a further missing function may be identified by the cloning of additional *V. harveyi* DNA into *E. coli* which already contains luxRCDABE on another replicon.

SUMMARY OF THE CONTROL SYSTEM TO DATE

1. There is low basal expression of luxI, the product of which makes autoinducer from cytosolic substrates.
2. cAMP/CRP activates the luxR promoter and luxR protein is produced.
3. LuxR protein interacts with autoinducer to form a complex (R/AI).
4. R/AI complex binds to lux operator region between luxR and luxI (perhaps displacing LexA or after LexA is cleaved due to SOS response).
5. Binding of R/AI promotes transcription of right operon (luxICDABE by $\sigma^{32}$ (htpR protein).

Although this invention is based on results rather than theory, the inventors currently believe that the compounds of formula 1 form a bacterial pheromone family which have a primary role in controlling various functions in bacteria and other microorganisms. These freely soluble and diffusable low molecular weight molecules may act as sensors of inter-microbial communication. As density sensors they may control initiation of maintenance gene expression (Sigma 32). Sensing isolation they may prevent expression of conjugative gene systems, and again sensing density, they may trigger the initial Sigma factor change in bacilli that precedes the sigma cascade during sporulation.

DETAILED DESCRIPTION

The following examples illustrate various aspects of the invention.

Example 1 describes a bioassay in which a mutant strain of *Erwinia carotovora* is used to detect autoinducer, or bacteria which generate autoinducer. The detectable phenotype in this case is carbapenem production.

Example 2 describes the isolation of N-(β-ketocaproyl) homoserine lactone from the culture supernatant of an *Erwinia carotovora* strain. This is of interest as a demonstration that a non-bioluminescent non-marine bacterium produces the autoinducer that controls the lux operon of *Vibrio fischeri*.

Example 3 describes the preparation of numerous mutants of the *E. carotovora* strain which lack the ability to make carbapenem antibiotics. The example demonstrates that in some of these mutants the antibiotic production capability can be restored by addition of exogenous autoinducer.

Example 4 describes a different bioassay for autoinducer, based on the genetic construct pSB237. A bioassay uses bioluminescence to test for the presence of autoinducer, or microorganisms that make it. Using the assay, many bacteria are identified as producers of the autoinducer.

Example 5 describes the preparation and characterisation of N-(β-ketocaproyl) homoserine lactone and analogues, both in the racemic form and as D- and L-isomers.

Example 6 describes a bioassay, along the lines of Example 1, to detect the analogues described in Example 5.

Example 7 describes a method for the enumeration of *Pseudomonas aeruginosa* using *E. coli* [pSB237] as an indicator strain.

Example 8 shows induction of carbapenem production by the L- and D-isomers of autoinducer.

Example 9 describes an experiment to demonstrate the action of autoinducer in enhancing the rate of growth of bacteria.

Example 10 demonstrates activity of various analogues in inducing luminescence.

Example 11 demonstrates early induction of carbapenem production by autoinducer in *E. carotovora*.

Example 12 shows the effect of autoinducer on the recovery of injured microorganisms.

EXAMPLE 1

Bioassay for Autoinducer

1. The bioassay method is based around an autoinducer non-producing, EMS generated mutant strain of *Erwinia carotovora*: B10 002/mu22, henceforth called by the abbreviated name: mutant 22 (whose preparation is described in Example 3). The biosynthesis of carbapenem antibiotic is induced by the autoinducer compound. Mutant 22 is blocked at some point in the biosynthesis of autoinducer. Thus, addition of a sample containing the autoinducer compound will complement this genetic lesion, allowing the biosynthesis of antibiotic observed in the strain from which the mutant is derived.

2. Samples of up to 50 μl in volume are added to wells of approximately 10 mm in diameter, cut in Oxoid DST agar plates seeded with an *E. coli* carbapenem super-sensitive strain (*E. coli* ESS). DST agar is made up as directed. After autoclaving, the DST agar is cooled to 45° C., then 3.0 ml per liter of DST agar of a culture of *E. coli* ESS added. The latter is grown up overnight in Oxoid brain heart infusion broth at 37° C.

3. An inoculum of Mutant 22 is placed around the rim of the wells containing the samples to be analysed for autoinducer. Positive and negative controls are included consisting of: i) antibiotic-producing strain (*Erwinia carotovora* ATCC 39048); ii) mutant 22 with synthetic autoinducer; iii) mutant 22 without any sample added; iv) and each sample tested for antibacterial activity in the absence of mutant 22 to test for presence of antibiotics or residual solvents.

4. The plates are inoculated overnight at 26° C. If the autoinducer is present in a sample placed in a well with mutant 22, the antibiotic produced gives a clearing on the plate.

EXAMPLE 2

Isolation of N-(β-ketocaproyl) homoserene lactone from the culture supernatant of *Erwinia carotovora* ATCC39048

*E. carotovora* was maintained on nutrient agar slopes. A loopfull of the culture was inoculated into seed stage medium (consisting of neutralised soya peptone 1% w/v and sucrose 0.1% w/v) and incubated at 26° C. on a rotary shaker for 24 hours. 1 ml was added to each of four Erlenmeyer flasks, each containing 500 ml production (ECP) medium. This consisted of:

| L-Glutamic acid | 0.2% w/v |
|---|---|
| Ammonium sulphate | 0.1% w/v |
| di-Potassium hydrogen orthophosphate | 0.37% w/v |
| Potassium di-hydrogen orthophosphate | 0.62% w/v |
| Sodium Chloride | 0.02% w/v |
| Casamino acids (Difco) | 0.2% w/v |
| Glucose | 0.4% w/v |
| Ferrous sulphate heptahydrate | 0.001% w/v |
| Magnesium sulphate heptahydrate | 0.01% w/v |

Cultures were incubated on a rotary shaker at 26° C., 220 rpm for 16 hours. Cultures were clarified by centrifugation (10,000 rpm, 10 minutes), supernatant taken and extracted twice with 400 ml ethyl acetate (distilled over potassium carbonate). The ethyl acetate layer was taken, 30 ml of distilled water added and ethyl acetate removed by rotary evaporation at 35° C.

The aqueous solution thus obtained was passed twice through a column which contained hydrophobic resin (Styrene-divinylbenzene copolymer CHP3C, Mitsubishi Ltd.). The column was eluted with distilled water (60 ml), then 30% v/v methanol in water (60 ml), then 70% v/v methanol in water (60 ml). Fractions were monitored throughout for biological activity using the Complementation Bioassay.

The 70% fraction (which contained all detectable biological activity) was taken and concentrated to a volume of 3 ml by rotary evaporation at 35° C. Further substantial purification was achieved by HPLC, set up as follows:

| Column | Semi-preparative, Reverse phase (S50DS2, Hi-Chrom Ltd.) |
|---|---|
| Mobile Phase | 15% v/v methanol in water |
| Flow Rate | 2 ml/min |
| Monitoring wavelength | 210 nm |
| Injection volume | 0.5 ml |

The autoinducer eluted at ca 17.5 minutes.

Fractions were pooled, methanol removed by rotary evaporation at 35° C., aqueous solution freeze dried to yield 1 mg 99+% pure N-(β-ketocaproyl) homoserine lactone as a lyophilised white powder.

EXAMPLE 3

Production of Autoinducer non-producing mutants in *Erwinia carotovora* ATCC 39048 using ethyl methane sulphonate (EMS) Mutagenesis 1. *Erwinia carotovora* ATCC 39048 is grown in LB medium (Maniatis et al., 1982) containing 10 μg/ml kanamycin, 50 μg/ml tetracycline in a rotary shaker at 26° C. overnight. $OD_{600}$ is measured to ensure culture has reached stationary phase ($OD_{600} \geq 2.0$).

2. Inoculate 1.0 ml of above culture into 50 ml of fresh complex medium. Place on rotary shaker at 26° C. Grow to $OD_{600} \approx 0.7$.

3. Centrifuge 1.0 ml of culture in a sterile microfuge tube at 12K rpm for 2 minutes at room temperature. Resuspend cells in 1.0 ml of sterile SPC buffer (SPC buffer: 0.15M NaCl, 10.8 mM $NaH_2PO_4$, 9.0 mM citric acid (pH 7.0)). Cells were pelleted as above, supernatant discarded and cells resuspended in 1.0 ml of sterile SPC buffer.

4. 25 μl of ethyl methane sulphonate (EMS) is added to 1.0 ml of cells suspended in SPC buffer, to give a 2.5% solution of EMS. Cells are then incubated with EMS without shaking for 1 hour at room temperature.

5. Centrifuge cells in a microfuge at 12 k rpm for 2 mins. Remove supernatant and resuspend cells in 1.0 ml of sterile 5% sodium thiosulphate (pH 7.0). Wash the cells with 1.0 ml of sterile SPC buffer twice to remove any traces of sodium thiosulphate.

6. Resuspend cells in 1.0 ml LB medium. Place in 26° C. incubator without shaking for 1 hour.

7. Dilutions of cells are made in sterile water and 100 μl volumes spread on nutrient agar plates containing 10 μg/ml kanamycin, 50 μg/ml tetracycline. Plates are incubated at 26° C. for 48 hours.

8. Colonies were picked-off the above plates using sterile toothpicks and an inoculum placed on DST agar plates seeded with *E. coli* ESS strain (Oxoid DST agar made up as directed. After autoclaving, agar is cooled to 45° C and 3.0 ml of an overnight culture of *E. coli* ESS strain in Oxoid brain heart infusion broth added to 1 liter of DST). Plates are incubated at 26° C. for 24 hours. When carbapenem antibiotic is produced by the Erwinia colony a clearing is observed. Non-producers of carbapenem antibiotic are selected. Amongst those are autoinducer non-producing mutant colonies (about 20% of the total showing a phenotype of antibiotic non-production).

9. Autoinducer non-producing mutant strains have been identified by complementation analysis using whole cells, filter sterilised culture supernatants and HPLC analysis of culture supernatants.

Complementation Test of Mutants

1. Using Oxoid DST agar seeded with *E. coli* supersensitive strain (ESS), it can be shown that some mutants derived from *Erwinia carotovora* ATCC 39048 are no longer able to synthesise carbapenem antibiotic. Amongst these are mutants unable to synthesise autoinducer which is a requirement for carbapenem biosynthesis. Due to the diffusable nature of the autoinducer molecule a mutant defective in the biosynthesis of the compound will be complemented by strains with mutations in the carbapenem biosynthetic pathway or regulatory autoinducer binding proteins, which will have the functional autoinducer biosynthetic machinery.

2. Complementation is observed by mixing whole cells of mutant strain B10 002/mutant 22 (subsequently called mutant 22) with other mutants such as mutant strain B11 001/mutant 26 (subsequently called mutant 26).

3. Mutants are mixed together on DST agar seeded with *E. coli* ESS. When mixed, production of antibiotic and concomitant clear zone on the plate are observed. Separate inoculums of each mutant do not produce any antibiotic.

4. The same effect can be observed when feeding filter-sterilised supernatant from a culture of one mutant to a mutant of a separate complementation group. A 50 μl sample is placed in a well cut in a DST agar plate seeded with *E. coli* ESS, with the chosen mutant inoculated around the rim of the well. The plate is incubated at 26° C. for 24 hours, after which time clear zones produced by the presence of antibiotic will be visible.

5. Feeding the supernatant from a mutant such as mutant 26 to mutant 22 induces antibiotic production in the latter. No induction of carbapenem is observed when filter-sterilised supernatant from mutant 22 is incubated with mutant 26 on bioassay plates.

The following Table lists the mutant strains prepared.

TABLE 1

Compilation of *Erwinia carotovora* strains with antibiotic non-producing phenotypes

| COMPLEMENTATION GROUP 1 | | | COMPLEMENTATION GROUP 2 | | |
|---|---|---|---|---|---|
| strain | number | mutagen used | strain | number | mutagen used |
| A05 002 | 8 | NTG | B03 001 | 4 | EMS |
| A05 003 | 9 | NTG | B10 002 | 22 | EMS |
| A05 005 | 10 | NTG | B10 003 | 23 | EMS |
| A05 020 | 11 | NTG | | | |
| A05 026 | 12 | NTG | | | |
| A06 001 | 13 | NTG | | | |
| A07 005 | 14 | NTG | | | |
| A07 037 | 15 | NTG | | | |
| A08 003 | 16 | NTG | | | |
| A08 004 | 17 | NTG | | | |
| A08 017 | 18 | NTG | | | |
| A08 020 | 19 | NTG | | | |
| A08 022 | 20 | NTG | | | |
| B10 001 | 21 | EMS | | | |
| B10 004 | 24 | EMS | | | |
| B10 005 | 25 | EMS | | | |

TABLE 1-continued

Compilation of *Erwinia carotovora* strains with antibiotic non-producing phenotypes

| B11 001 | 26 | EMS |
|---|---|---|

The first three digits of the mutant strain number indicate individual *mutagenesis* experiments.

| | COMPLEMENTATION GROUP 1 | COMPLEMENTATION GROUP 2 |
|---|---|---|
| Total number of mutants produced | 17 | 3 |

EXAMPLE 4

The construction of pSB 237: a. *V. fischeri* autoinducer sensor controlling a bioluminescent phenotype in *E. coli*

An *E. coli* vector pSB226 containing a promoterless copy of the luxA and luxB genes from *V. harveyi* has been previously described (Hill et al., 1991)

This vector has a unique EcoR1 site proximal to luxA which facilitates the insertion of promoterless elements. A luxR lux promoter region of the *V. fischeri* lux operon was obtained by PCR using the following primers designed to incorporate terminal EcoR1 sites and to have homology to sequences previously identified by Engebrecht and Silverman (1987).

```
Primer (1) (5' end of luxR)
5'                                                              3'
AAG CTT GAATTC CCG GGT TAA TTT TTA AAG TAT GGG CAA TCA ATT (SEQ. ID NO: 1)
Primer (2) (3' end of lux promoter)
5'                                                              3'C
TTT TAT GAATTC TAC GTA ACC AAC CTC CCT TGC GTT TAT TCG A (SEQ. ID NO: 2)
```

Recognition sequences for EcoR1 are underlined.

The PCR fragment obtained by use of the above primers was digested with EcoR1 and inserted into the unique EcoR1 site of pSB226. Recombinant clones were selected on the basis of a bioluminescent phenotype dependent upon the presence of dodecanal vapour and synthetic *V. fischeri* autoinducer. One such recombinant was designated pSB237.

This example uses *E. coli* [pSB237], a bacterium in which, as noted above, bioluminescence is expressed only in the presence of exogenous N-(β-ketocaproyl) homoserine lactone (or analogue). This phenotype is used as a basis of a test for synthetic autoinducer or for other bacteria that may produce autoinducer.

Bioluminescent bioassay for autoinducer

The bioassay method is based on *E. coli* [pSB237], described above. Overnight LB cultures (Maniatis et al., 1982) of *E. coli* [pSB237] are used to initiate exponential cultures by appropriate dilution into fresh LB media. 100 μl of exponential cultures are placed into microtitre wells within a microtitre tray format. 100 μl of cell free culture supernatant or appropriately diluted N-(β-ketocaproyl) homoserine lactone is added individually to wells so that the potential to induce bioluminescence from *E. coli* [pSB237] can be assessed. Microtitre trays are incubated at 30° C. prior to bioluminescence determination which must be preceded by the addition to each well of 5 μl of a 1% dodecanal solution in ethanol. The limits for detection of autoinducer using a bioluminescent phenotype derived from *E. coli*

[pSB237] depend upon the time of exposure of the bacterial culture to inducer. At concentrations above 10 ng/ml of culture, induction of bioluminescence is rapid (less than 10 min). At lower concentrations induction is progressively slower but concentrations as low as 80 pg/ml can be distinguished from a zero concentration control after some 20 h of incubation (FIG. 2). This establishes the bioluminescent assay as a highly sensitive and simple monitor of inducer.

*Pseudomonas aeruginosa*

*P. aeruginosa* produces complementing activity (confirmed as autoinducer) only under defined growth conditions. In rich media such as LB or Brain Heart Infusion Broth the degree of complementing activity is low. In limiting or minimal growth media and particularly when supplemented with 1 mg/ml Fe(III), the production of complementing activity is very considerable. By comparison with standard concentrations of autoinducer (L-isomer), the supernatant of such a *P. aeruginosa* culture could be estimated to contain some 10 ng/ml of autoinducer. The media dependency of complementation activity strongly suggests that production is regulated and that under favourable conditions production levels may equate to those previously reported in marine bacteria (Eberhard, 1981; 1 μg/ml).

*Serratia marcescens*

*S. marcescens* is capable of providing a similar level of complementing activity for *E. coli* [pSB237] as *P. aeruginosa*. the major difference is that in this instance there is no media variability with very high complementations achieved from BHI supernatants. This would suggest constitutive expression of autoinducer, a feature previously described for *V. fischeri* (Eberhard et al., 1981).

*Proteus mirabilis* and *Citrobacter freundii*

Both of these bacteria produce complementing activity in a limiting growth medium (CCY; Stewart et al., 1981). The activity detailed by the bioluminescent assay indicates a lower level of inducer formation or, alternatively, production of an inducer analogue with lower activity for the luciferase luxR product. Nevertheless, the rate of appearance of activity would reflect inducer levels of greater than 1 ng/ml for a homologous compound.

Microorganisms with low but detectable activities

Table 2 and the accompanying FIG. 3 list microorganisms that provide complementation for activation of bioluminescence with *E. coli* [pSB237]. Typically, activity can take between 0.5 and 6 hours to become measurable above background controls. Given the dependence upon time for detection of low levels of autoinducer, it is possible that these long incubation periods reflect low levels of inducer in the microbial cultures. It is particularly interesting to note that almost none of the cultures provided any complementing activity in rich media but that the limiting CCY media was particularly productive.

It is possible that the production of inducer analogues of low intrinsic activity with *E. coli* [pSB237] could be an alternative explanation of the above but equally these results could reflect the detection of basal levels of autoinducer production. These could, after appropriate physiological trigger events, be switched to high production for gene control functions.

Other tests have shown positive results (i.e. production of autoinducer) also by the following microorganisms: *Hafnia alvei, Serratia liquefaciens, Enterobacter agglomerans*, and *Rahnella aguatilis*.

TABLE 2

| | | | |
|---|---|---|---|
| $A_1$ | *Aeromonas hydrophila* | $A_2$ | *Citrobacter freundii* 6071 |
| $B_1$ | CONTROL | $B_2$ | *Citrobacter freundii* 9756 |
| $C_1$ | *Bacillus cereus* | $C_2$ | *Citrobacter koseri* 10849 |
| $D_1$ | *Bacillus coagulans* | $D_2$ | *Bacillus coagulans* |
| $E_1$ | *Bacillus megaterium* | $E_2$ | *Bacillus cereus* 866 |
| $F_1$ | *Bacillus megaterium* KM | $F_2$ | *Bacillus licheniformis* |
| $G_1$ | *Bacillus subtilis* | $G_2$ | *Bacillus macerans* |
| $H_1$ | *Brochothrix thermosphacta* | $H_2$ | *Bacillus megaterium* 9885 |
| $A_3$ | *Bacillus pumilis* | $A_4$ | *Alcaligenes faecalis* |
| $B_3$ | *Bacillus subtilis* 2129 | $B_4$ | *Klebsiella aerogenes* |
| $C_3$ | *Bacillus subtilis var niger* | $C_4$ | *Listeria grayii* |
| $D_3$ | *Bacillus globigii* | $D_4$ | *Listeria monocytogenes* 4859 |
| $E_3$ | *Escherichia coli* 86 | $E_4$ | *Listeria moncytogenes* 23074 |
| $F_3$ | *Enterobacter aerogenes* | $F_4$ | *Listeria monocytogenes* 5348 |
| $G_3$ | *Enterobacter cloacae* | $G_4$ | *Micrococcus luteus* |
| $H_3$ | *Erwinia herbicola* | $H_4$ | CONTROL |
| $A_5$ | *Proteus mirabilis* | $A_6$ | *Pseudomonas putida* JT1 |
| $B_5$ | *Proteus vulgaris* | $B_6$ | *Salmonella arizonae* |
| $C_5$ | CONTROL | $C_6$ | *Salmonella infantis* |
| $D_5$ | *Pseudomonas aeruginosa* PA01 (KILLED) | $D_6$ | *Salmonella montevideo* |
| $E_5$ | *Pseudomonas fluorescens* | $E_6$ | *Salmonella typhimurium* LT2 |
| $F_5$ | *Pseudomonas putidas* | $F_6$ | *Serratia marcescens* (KILLED) |
| $G_5$ | *Pseudomonas putida* 340 | $G_6$ | *Streptococcus faecalis* |
| $H_5$ | *Pseudomonas putida* IC4A | $H_6$ | *Streptococcus pyogenes* |
| $A_7$ | *Streptococcus mutans* | | |
| $B_7$ | CONTROL | | |
| $C_7$ | CONTROL | | |
| $D_7$ | *Staphylococcus aureus* | | |
| $E_7$ | *Vibrio cholerae* non 01 | | |
| $F_7$ | *Escherichia coli* K12 | | |
| $G_7$ | 5 ng autoinducer (KILLED) | | |
| $H_7$ | — | | |

EXAMPLE 5

Synthesis of the Complementation Factor (Autoinducer) [N-(3-oxohexanoyl)-L-homoserine lactone] and its analogues 1. Synthesis of N-(3-oxoalkanoyl)homoserine lactones (Compounds No. 1, 2, 3, 4, 14, 15 and 16)
General Method Triethylamine (1 mmol) was added to a stirred solution of homoserine lactone hydrochloride (the L- or D-isomer or a racemic mixture) (1 mmol) in water (2 ml) followed by the addition of ethylene glycol ketal of 3-oxoalkanoic acid (1 mmol) and 1-ethyl-3-(3-dimethylaminopropyl)carbodiimide hydrochloride (1 mmol). The mixture was stirred for 20 h and then rotary evaporated to dryness at about 35° C. The light orange residue was extracted with warm ethyl acetate (5×5 ml) and the extracts pooled and washed successively with water (1×3 ml), 5% sodium bicarbonate solution (1×3 ml), 1M potassium hydrogen sulphate solution (1×3 ml) and finally brine (1×5 ml). Drying (MgSO$_4$) and evaporation of solvent in vacuo gave the ethylene glycol ketal of 3-oxoalkanoylated homoserine lactones (40–50%).

Perchloric acid (60%, 0.25 ml) was added to an ice-cooled solution of the alkanoylated lactone (0.5 mmol) in dichloromethane (15 ml). The mixture was stirred at 0° C. for 0.5 h and then at room temperature for 1.5 h. The solvent was removed in vacuo and the residue redissolved in ethyl acetate (20 ml). The solution was washed with cold water (2×5 ml) and brine (1×5 ml), dried (MgSO$_4$) and rotary evaporated to obtain the desired N-(3-oxoalkanoyl)homoserine lactones (55–60%).

Compound 16 is derived from homocysteine lactone instead of homoserine lactone.

2. Synthesis of N-acylated homoserine lactone (Compounds No. 5, 6, 7, 8 and 9)

General Method

Triethylamine (1 mmol) was added to a stirred solution of homoserine lactone hydrochloride (the L- or D-isomer or a racemic mixture) (1 mmol) in water (2 ml) followed either by the addition of acid anhydride (3 mmol) (compounds 5, 6 and 7) or acid (1.5 mmol) and 1-ethyl-3-(3-dimethylaminopropyl)carbodiimide hydrochloride (1.5 mmol) (compounds 8 and 9). The mixture was stirred at room temperature overnight and then evaporated in vacuo to dryness. The residue was partitioned between water (5 ml) and ethyl acetate (20 ml) and the organic layer successively washed with 5% NaHCO$_3$ solution (2×5 ml), 1M KHSO$_4$ solution (1×5 ml) and brine (1×5 ml). Drying (MgSO$_4$) and removal of solvent gave the title acylated lactones (20–60%).

3. Synthesis of N-(3-hydroxyalkanoyl)-L-homoserine lactones (Compounds 10, 11, 12 and 13)

General Method

N-(3-Oxoalkanoyl)-L-homoserine lactone (0.2 mmol) was dissolved in methanol (5 ml) and the solution made acidic (pH 3–4) with 2M HCl-methanol. Sodium cyanoborohydride (0.5 mmol) was added in one lot with stirring and the reaction mixture maintained at pH 3–4 by the occasional addition of 2M HCl-methanol. After 2 h, solvent was removed in vacuo and ethyl acetate extracts (3×5 ml) of the residue were combined, dried (MgSO$_4$) and evaporated to yield the title hydroxy derivatives. The products were purified by preparative layer chromatography on silica plates in CHCl$_3$—MeOH (9:1) and repurified by HPLC. The latter also resolved and separated the diastereoisomers in the case of compounds 10 and 11.

Autoinducer and its analogues prepared by these methods were more than 90% pure and were further purified with reverse phase HPLC using a 1×25 cm S50DS2 semi-prep column eluting isocratically with 15–20% MeOH—H$_2$O mixture and monitoring at 210 nm. The products were freeze-dried and stored below 0° C.

All the compounds (see Table 3) were characterised by i.r., mass spectra (EI) and high field n.m.r. as follows.

Compound 1 [N-(3-oxohexanoyl)-L-homoserine lactone]

$v_{max}$ (KBr) 3295 (NH), 1780 (ring C=O), 1710 ketone C=O), 1650 (amide C=O), 1550, 1170 cm$^{-1}$.

m/z (EI) (%) 213.0989 (47, M$^+$, C$_{10}$H$_{15}$NO$_4$ requires m/z 213.1001), 185 (13), 170 (8), 155 (7), 143 (33), 128 (8), 113 (19), 102 (56), 101 (35), 71 (82), 57 (100).

$\delta_H$ (CDCl$_3$) (400 MHZ) 0.9 (3H, t, CH$_3$), 1.64 (2H, sextet, CH$_3$.C$\underline{H}_2$), 2.22 (1H, dddd, 4α-H), 2.51 (2H, t, CH$_2$.CO), 2.77 (1H, ddd, 4β-H), 3.47 (2H, s, CO.CH$_2$.CO), 4.28 (1H, ddd, 5α-H), 4.48 (1H, dd, 5β-H), 4.59 (1H, ddd, 3-H), 7.65 (1H, bs, NH).

$\delta_{13C}$ (CDCl$_3$) 13.58 (CH$_3$), 16.91 (CH$_2$), 29.94 (CH$_2$), 45.85 (CH$_2$), 28.13 (CH$_2$), 49.12 (CH), 65.94 (CH$_2$), 166.38 (CO.NH), 174.83 (ring C=O), 206.54 (C=O).

Compound 3 [N-(3-oxopentanoyl)-L-homoserine lactone]

$v_{max}$ (KBR) 3280 (NH), 1780 (ring C=O), 1710 (ketone C=O), 1645 (amide C=O), 1550, 1170 cm$^{-1}$.

m/z (EI) (%) 199.0845 (25, M$^+$, C$_9$H$_{13}$NO$_4$ requires m/z 199.0845), 170 (9), 154 (7), 141 (6), 125 (7), 102 (34), 101 (34), 57 (100), 43 (36).

$\delta_H$ (CDCl$_3$) (400 MHz) 1.09 (3H, t, CH$_3$), 2.23 (1H, dddd, 4α-H), 2.57 (2H, q, CH$_3$.C$\underline{H}_2$), 2.77 (1H, ddd, 4β-H), 3.48 (2H, s, CO.CH$_2$.CO), 4.28 (1H, ddd, 5α-H), 4.48 (1H, dd, 5β-H), 4.58 (1H, ddd, 3-H), 7.60 (1H, bs, NH).

Compound 4 [N-(3-oxobutanoyl)homoserine lactone]

$v_{max}$ (KBr) 3280 (NH), 1780 (ring C=O), 1710 (ketone C=O), 1640 (amide C=O), 1550, 1170 cm$^{-1}$.

m/z (EI) (%) 185.0701 (3, M$^+$, C$_8$H$_{11}$NO$_4$ requires m/z 185.0687), 140 (4), 127 (7), 102 (4), 101 (21), 57 (72), 43 (100).

$\delta_H$ (CDCl$_3$) (400 MHz) 2.23 (1H, dddd, 4α-H), 2.28 (3H, s, CH$_3$), 2.77 (1H, ddd, 4β-H), 3.50 (2H, s, CO.Ch$_2$.CO), 4.28 (1H, ddd, 5α-H), 4.48 (1H, dd, 5β-H), 4.59 (1H, ddd, 3-H) 7.60 (1H, bs, NH).

Compound 6 [N-butanoyl-L-homoserine lactone]

$v_{max}$ (KBr) 3310 (NH), 1775 (ring C=O), 1640 (amide C=O), 1545, 1175 cm$^{-1}$.

m/z (EI) (%) 171.0922 (12, M$^+$, C$_8$H$_{13}$NO$_3$ requires m/z 171.0896), 153 (4), 143 (65), 128 (5), 125 (5), 102 (10), 101 (10), 71 (57), 57 (65), 43 (100).

$\delta_H$ (CDCl$_3$) (400 MHz) 0.96 (3H, t, CH$_3$), 1.68 (2H, sextet, CH$_3$.C$\underline{H}_2$), 2.19 (1H, dddd, 4α-H), 2.24 (2H, t, CH$_2$.CO), 2.82 (1H, ddd, 4β-H), 4.29 (1H, ddd, 5α-H), 4.47 (1H, dd, 5β-H), 4.59 (1H, ddd, 3-H), 6.26 (1H, bs, NH).

Compound 7 [N-acetyl-L-homoserine lactone]

$v_{max}$ (KBr) 3300 (NH), 1785 (ring C=O), 1640 (amide C=O), 1535, 1185 cm$^{-1}$.

m/z (EI) (%) 143.0546 (6, M$^+$, C$_6$H$_9$NO$_3$ requires 143.0582), 125 (5), 116 (2), 101 (3), 98 (11), 57 (93), 43 (100).

$\delta_H$ (CDCl$_3$) (400 MHz) 2.06 (3H, s, CH$_3$), 2.19 (1H, dddd, 4α-H), 2.78 (1H, ddd, 4β-H), 4.29 (1H, ddd, 5α-H), 4.47 (1H, dd, 5β-H), 4.62 (1H, ddd, 3-H), 6.57 (1H, bs, NH).

Compound 8 {N[(E)-hex-2-enoyl]-L-homoserine lactone}

$v_{max}$ (KBr) 3310 (NH), 1780 (ring C=O), 1675 (amide C=O), 1635 (C=C), 1555, 1175 cm$^{-1}$.

m/z (EI) (%) 197.1088 (11, M$^+$, C$_{10}$H$_{15}$NO$_3$ requires m/z 197.1052), 154 (9), 97 (100), 85 (3).

$\delta_H$ (CDCl$_3$) (400 MHz) 0.94 (3H, t, CH$_3$), 1.48 (2H, sextet, CH$_3$.C$\underline{H}_2$), 2.17 (3H, m. 4α-H and C$\underline{H}_2$.CH=CH), 2.86 (1H, m, 4β-H), 4.31 (1H, ddd, 5α-H), 4.48 (1H, dd, 5β-H), 4.63 (1H, ddd, 3-H), 5.83 (1H, dt, CH=C$\underline{H}$.CO), 6.11 (1H, d, NH), 6.90 (1H, dt, C$\underline{H}$=CH.CO).

Compound 9 [N-hexanoyl-L-homoserine lactone]

$v_{max}$ (KBr) 3315 (NH), 1775 (ring C=O), 1645 (amide C=O), 1550, 1175 cm$^{-1}$.

m/z (EI) (%) 199.1256 (5, M$^+$, C$_{10}$H$_{17}$NO$_3$ requires m/z 199.1208), 170 (5), 156 (8), 143 (100), 85 (10).

$\delta_H$ (CDCl$_3$) (90 MHz) 0.87 (3H, t, CH$_3$), 1.0–1.40 (4H, m, CH$_3$.C$\underline{H}_2$.C$\underline{H}_2$), 1.40–1.85 (2H, m, C$\underline{H}_2$.CH$_2$.CO), 1.85–2.45 (3H, m, C$\underline{H}_2$.CO and 4α-H), 2.45–2.90 (1H, m, 4β-H), 4.0–4.75 (3H, m, 5-H$_2$ and 3-H), 6.43 (1H, d, NH).

Compound 10 {N-[(S)-3-hydorxyhexanoyl]-L-homoserine lactone} m/z (EI) (%) 197.0995 (9, M$^+$-H$_2$O, C$_{10}$H$_{15}$NO$_3$ requires m/z 197.1052), 172.0629 (52, M$^+$-C$_3$H$_7$, C$_7$H$_{10}$NO$_4$ requires m/z 172.0610), 154 (4), 143 (31), 102 (100).

δ$_H$ (CDCl$_3$) (400 MHz) 0.94 (3H, t, CH$_3$), 1.44 (2H, m, CH$_3$.C$\underline{H}_2$), 1.55 (2H, m, C$\underline{H}_2$.CH.OH), 2.18 (1H, dddd, 4α-H), 2.35 (1H, dd, C$\underline{H}_\alpha$H$_\beta$.CO), 2.44 (1H, dd, CH$_{\alpha}$$\underline{H}_\beta$.CO), 2.83 (1H, dddd, 4β-H), 3.07 (1H, br s, OH), 4.04 (1H, dddd, C$\underline{H}$OH), 4.28 (1H, ddd, 5α-H), 4.48 (1H, ddd, 5β-H), 4.57 (1H, ddd, 3-H), 6.55 (1H, br s, NH).

Compound 11 {N-[(R)-3-hydroxyhexanoyl]-L-homoserine lactone} m/z (EI) (%) 197.1066 (11, M$^+$-H$_2$O, C$_{10}$H$_{15}$NO$_3$ requires m/z 197.1052), 172.0612 (53, M$^+$-C$_3$H$_7$, C$_7$H$_{10}$NO$_4$ requires m/z 172.0610), 143 (27), 102 (100).

δ$_H$ (CDCl$_3$) (400 MHz) 0.94 (3H, t, CH$_3$), 1.43 (2H, m, CH$_3$.C$\underline{H}_2$), 1.55 (2H, m, C$\underline{H}_2$.CH.OH), 2.19 (1H, dddd, 4α-H), 2.33 (1H, dd, C$\underline{H}_\alpha$H$_\beta$CO), 2.46 (1H, dd, CH$_\alpha$$\underline{H}_\beta$.CO), 2.83 (1H, dddd, 4β-H), 4.05 (1H, dddd, C$\underline{H}$.OH), 4.30 (1H, ddd, 5α-H), 4.48 (1H, ddd, 5β-H), 4.55 (1H, ddd, 3-H), 6.50 (1H, br s, NH).

Compound 12 {N-[(RS)-3-hydroxypentanoyl]-L-homoserine lactone} m/z (EI) (%) 201.0939 (2, M$^+$, C$_9$H$_{15}$-NO$_4$ requires m/z 201.1001), 183.0931 (8, M$^+$-H$_2$O, C$_9$H$_{13}$NO$_2$ requires m/z 183.0895), 172.0677 (24, M$^+$-C$_2$H$_5$, C$_7$H$_{10}$NO$_4$ requires m/z 172.0610), 143 (28), 102 (44), 101 (32), 57 (100).

δ$_H$ (CDCl$_3$) (90 MHz) 0.93 (3H, t, CH$_3$), 1.50 (2H, quintet, CH$_3$.C$\underline{H}_2$), 2.15 (1H, m, 4α-H), 2.33 (2H, d, CH$_2$.CO), 2.60 (1H, m, 4β-H), 2.70 (1H, br s, D$_2$O exchangeable, OH), 4.0–4.80 (3H, m, 5-H$_2$ and 3-H), 6.90 (1H, br s, D$_2$O exchangeable, NH).

Compound 13 {N-[(RS)-3-hydroxybutyryl]-L-homoserine lactone} m/z (EI) (%) 187.0820 (2, M$^+$, C$_8$H$_{13}$NO$_4$ requires m/z 187.0844), 172.0614 (11, M$^+$-CH$_3$, C$_7$H$_{10}$NO$_4$ requires m/z 172.0610), 169.0761 (6, M$^+$-H$_2$O, C$_8$H$_{11}$NO$_3$ requires m/z 169.0739), 143 (34), 102 (46), 101 (18), 57 (100).

δ$_H$ (D$_2$O) (90 MHz) 1.20 (3H, d, CH$_3$), 2.20 (1H, m, 4α-H), 2.40 (2H, d, C$\underline{H}_2$.CO), 2.57 (1 H, m, 4α-H), 4.0–4.70 (4H, m, 5-H$_2$, 3-H and C$\underline{H}$.OH).

Compound 14 [N-benzoylacetyl-L-homoserine lactone]

m/z (EI) (%) 247.0824 (24, M$^+$, C$_{13}$H$_{13}$NO$_4$ requires m/z 247.0844), 147 (12), 105 (100), 77 (37).

δ$_H$ (CDCl$_3$/DMSO-d$_6$) (90 MHz) 2.20–2.80 (2H, m, 4-H$_2$), 3.94 (2H, s, CO.C$\underline{H}_2$.CO), 4.10–4.80 (3H, m, 5-H$_2$ and 3-H), 7.30–7.70 (3H, m, ArH), 7.95 (2H, dd, ArH), 8.56 (1H, d, NH).

TABLE 3

Autoinducer and its analogues

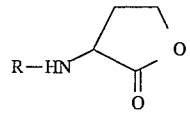

| No. | R | Chirality at C-3 | Overall Yield from Homoserine Lactone |
|---|---|---|---|
| 1 | CH$_3$.CH$_2$.CH$_2$.CO.CH$_2$.CO | L | 25% |
| 2 | CH$_3$.CH$_2$.CH$_2$.CO.CH$_2$.CO | D | 26% |
| 3 | CH$_3$.CH$_2$.CO.CH$_2$.CO | L | 28% |
| 4 | CH$_3$.CO.CH$_2$.CO | D,L | 28% |
| 5 | CH$_3$.CH$_2$.CH$_2$.CO | D,L | 39% |
| 6 | CH$_3$.CH$_2$.CH$_2$.CO | L | 40% |
| 7 | CH$_3$.CO | L | 20% |
| 8 | CH$_3$.CH$_2$.CH$_2$.CH=CH.CO | L | 35% |
| 9 | CH$_3$.CH$_2$.CH$_2$.CH$_2$.CH$_2$.CO | L | 60% |
| 10 | (S)—CH$_3$.CH$_2$.CH$_2$.CH(OH).CH$_2$.CO | L | 5% |
| 11 | (R)—CH$_3$.CH$_2$.CH$_2$.CH(OH).CH$_2$.CO | L | 5% |
| 12 | (RS)—CH$_3$.CH$_2$.CH(OH).CH$_2$.CO | L | 8% |
| 13 | (RS)—CH$_3$.CH(OH).CH$_2$.CO | L | 7% |
| 14 | Ph.CO.CH$_2$.CO | L | 20% |
| 15 | CH$_3$.CH$_2$.CH$_2$.CH$_2$.CO.CH$_2$.CO | | |
| 16* | CH$_3$.CH$_2$.CH$_2$.CO.CH$_2$.CO | | |

*In this compound the ring oxygen atom is replaced by sulphur

EXAMPLE 6

Erwinia mutant PNP22 was inoculated around the rims of 3 mm wells cut into agar plates seeded with E. coli ESS. Solutions of a range of concentrations of each analogue of Example 5 were prepared in distilled water, filter sterilised and 50 μl added to each well. Plates were incubated at 26° C. overnight and the resulting inhibition zone diameters measured (mm). FIG. 4 is a graph of inhibition zone diameter (which denotes induction of carbapenem antibiotic production) against concentration of various compounds. The dose response curves are shown for compounds 1, 14, 3, 11, 12, 9, 10 and 6. The remaining compounds in the series showed little or no activity in this assay, apart from the D isomer which shows about 10% activity (data not shown).

EXAMPLE 7

The enumeration of Pseudomonas aeruginosa using E. coli [DSB237] as an indicator strain.

A method for the enumeration of Pseudomonas aeruginosa was investigated using E. coli [pSB237] (FIG. 5) as an indicator. pSB237 confers an autoinducer-dependent bioluminescent phenotype on E. coli (upon addition of exogenous aldehyde) and can therefore detect the production of autoinducer from P. aeruginosa. The experiment requires an over-night culture of P. aeruginosa which is subjected to 10 fold serial dilutions such that approximately 2, 20 and 200 colonies are filtered onto a nitrocellulose membrane. We have found the use of membranes to be preferable to pour plate methods because the membranes provides an aerobic environment for the Pseudomonas to grow. The membranes are placed onto a lawn of E. coli [pSB237]. The inducer from P. aeruginosa diffuses through the membrane and triggers bioluminescence in localised areas of the E. coli [pSB237] lawn equivalent in size to the Pseudomonas colony. The number of light areas exactly correlate with the number of Pseudomonas colonies. In a mixed culture only those bacterial colonies which produce autoinducer will provide light in the *E. coli* [pSB237] lawn and this can, therefore, provide a very clear discrimination between what may otherwise be closely related bacteria.

Experimental details

1. Overnight cultures of *P. aeruginosa* PAO1 and *E. coli* [pSB237] were grown in Luria Broth.

2. A 10 fold dilution series of the overnight Pseudomonas culture was prepared using Luria Broth and samples plated onto Luria Broth Agar to obtain colony counts.

3. 0.5 ml of the overnight *E. coli* [pSB237] was added to 4 ml of molten (45° C.) Luria Broth Agar and spread onto a Luria Broth Agar plate.

4. 1 ml of the Pseudomonas dilution series -8, -7 and -6 (in duplicate) were individually filtered onto a Gelman 0.45 μm nitrocellulose membrane. These were subsequently individually placed onto *E. coli* [pSB2237] agar lawns as prepared in (3) above.

5. Plates were incubated at 30° C. for several hours and viewed with the Hamamatsu Argus 100 Vim 3 camera after exposure to nonanal vapour.

Results

| Dilution | No. of Light Areas | No. of colonies |
|---|---|---|
| −6 | Too many to count | Too many to count |
| −7 | 170/168 | 158/182 |
| −8 | 23/22 | 21/22 |

EXAMPLE 8

Induction of carbapenem biosynthesis in liquid culture

A culture of mutant PNP22 was grown overnight in ECP medium and a 2% inoculum (v/v) added to 100 ml of fresh ECP medium. This was incubated on a rotary shaker (rpm 220) at 26° C. for 6 hours (until OD>2.0).

Carbapenem HPLC assay

Bacteria were harvested by centrifugation at 10000 rpm for 10 mins. The supernatant was extracted with a solution of 4% Aliquat 336 (Aldrich) in distilled dichloromethane. Samples were analysed by HPLC using a reverse phase, semi-preparative column.

Induction of carbapenem biosynthesis in PNP22 by addition of exogenous autoregulator Synthetically produced autoregulator was added at a range of concentrations from 0 to 75 μg/ml and a dose-response curve constructed. The threshold for induction of carbapenem production is approximately 0.5 μg/ml. The optimum concentration is 1.0 μg/ml. Above this concentration, biosynthesis of carbapenem appears to be inhibited.

The experiment was repeated using the D-isomer in place of the L-isomer (i.e. compound 2 from Example 5 in place of compound 1). In this case the threshold for induction of carbapenem production was about 2 μg/ml and the optimum concentration was 30 μg/ml.

EXAMPLE 9

Effect of Autoinducer in microbial media on promoting microorganism metabolism

The measurement of microorganism metabolism can be monitored by several methods one of which is known as impedance monitoring. It has been shown that when bacteria grow in culture media the end products of metabolism are generally more highly charged than the original growth substrates. The resulting changes in impedance can be monitored and "growth" or metabolism curves constructed. The curves obtained by growth in different substrates can be compared for the growth quality of the substrates. The curves can also be used to determine the number of bacteria in a given sample, estimate the sensitivity of microorganisms to inhibitory substances such as antibiotics and also determine the utilisation of growth substances.

Experimental

Experiments were performed to examine the effects of autoinducer in culture media on the curves obtained using a Malthus AT growth analyser.

Serial tenfold dilution of a 4 hour culture in nutrient broth (Lab M, lab 14) of *Serratia marcescens* were prepared in sterile 0.9% saline. 0.02 ml of $10^{-4}$ or $10^{-5}$ dilution were added to 6 tubes of media as detailed below. The tubes were mixed and then attached to the Malthus system.

Easter & Gibson media (Lab M, lab 137) was used throughout with 5 g per liter tri-methyl amine N-oxide added before autoclaving. Sodium biselenite was omitted and the medium was prepared according to the manufacturer's instructions. The inducer (a synthetic preparation of N-(β-ketocaproyl) homoserine lactone) solution was prepared in sterile water and added to the Malthus tubes to give varying final concentrations up to 80 ng/ml.

8 of 9 sets of experiments showed an increase of maximum output of between 300–500 microsiemens at various concentrations of autoinducer (as compared to the increase of maximum output shown at zero autoinducer). These results clearly demonstrate that increased bacterial growth was obtained in the presence of inducer.

EXAMPLE 10

Activity of various analogues in inducing luminescence

Autoinducer and various analogues described in Table 3 were tested for their ability to induce luminescence in *E. coli* [pSB237] in the assay described in Example 4.

| Compound | Light Levels |
|---|---|
| 1 | +++ |
| 3 | ++ |
| 12 | ++ |
| 6 | + |
| 8 | + |

In another experiment, tenfold dilutions of autoinducer and various analogues were tested for their ability to induce luminescence in *E. coli* [psB237]. The following results were obtained, expressed as light levels as above:

| | Compound | | |
|---|---|---|---|
| Dilution | 1 | 15 | 16 |
| −2 | ++++ | +++ | ++++ |
| −3 | ++++ | +++ | ++++ |
| −4 | +++ | ++++ | ++++ |
| −5 | + | ++++ | + |
| −6 | − | ++++ | − |

EXAMPLE 11

Early Induction of Carbapenem Production by Autoinducer in *Erwinia carotovora* ATCC 39048

*Erwinia carotovora* ATCC 39048 was grown as in Example 2, except that 1 ml of overnight seed culture was inoculated into 50 ml ECP with and without autoinducer at a final concentration of 5 µg/ml. The cultures were incubated at 26° C. on a shaking incubator at 240 rpm. 100 µl samples of supernatant were taken and injected onto a Spherisorb S50DS2 HPLC column eluted with 100 mM $KH_2PO_4$ at 2 ml/min. The carbapenem peak eluted at approximately 7.8 minutes and was determined by absorbance at 254 nM. Inclusion of autoinducer switched on carbapenem production (3–6 hr) several hours earlier than control cultures (5–8 hr).

EXAMPLE 12

Effects on recovery of injured organisms
Aim
To test the effect of Autoinducer on recovery on selective and non-selective agar of *Serratia marcescens* bacteria with freezing induced injuries.
Materials
Overnight culture of *Serratia marcescens* grown in Luria Broth, static at 37° C.
Maximum Recovery Diluent (MRD) (Oxoid CM733, Lot No. 203 40764) made up according to manufacturers instructions.
Plates of Luria Agar (LA).
Plates of Violet Red Bile Glucose Agar (VRBGA) (Oxoid CM485, Lot No. 138 40768) made up according to manufacturers instructions.
Autoinducer stock: DL-N-(3-oxohexanoyl)-L-homoserine lactone 10 mg/ml in ethyl-acetate.
Method
Plates with 20 ng Autoinducer/ml agar were prepared in the following way:
Autoinducer solution 4 µg/ml was prepared by mixing 4 µl stock with 10 ml Maximum Recovery diluent.
Pre-poured, dried agar plates were weighted to nearest 2 g, and 5 µl Autoinducer solution/g agar was dispensed and spread on the surface using a sterile, disposable L-shaped spreader. Plates were then stored overnight at 4° C. in the dark before drying prior to use.
Control plates without Autoinducer were prepared in a similar fashion substituting sterile Maximum Recover Diluent for Autoinducer solution.
The overnight culture was diluted in 10-fold serial dilutions to $10^{-4}$ in sterile Bijou's by mixing 500 µl culture+ 4500 µl MRD (=$10^{-1}$), 500 µl $10^{-1}$+4500 µl MRD (=$10^{-2}$) 500 µl $10^{-3}$ dilution+4500 µl MRD (=$10^{-4}$).
The $10^{-4}$ dilution was used in the further work as working suspension.
Controls
100 µl working suspension was serially diluted as described in 1000 µl volumes, and 100 µl of the resulting dilutions $10^{-1}$, $10^{-2}$ and $10^{-3}$ were surface plated in duplicate on each of the following media:
  Luria Agar (LA)
  Luria Agar+20 ng Autoinducer (LA+I)
  Violet Red Bile Glucose Agar (VRBGA)
  Violet Red Bile Glucose Agar+20 ng Autoinducer (VRGBA+I)
Freeze-shocked samples
The remaining 4900 µl of working suspension was transferred to a freezer and stored at −21° C. After 210 minutes this was thawed in a waterbath at 31.5° C. for 15 minutes, and duplicates of 100 µl of the thawed working solution and a $10^{-1}$ dilution in MRD of the thawed working solution were plated on the 4 agars as described.

Plates were counted after incubation at 22° C. for 24 and 48 hrs.
Results
Results are given as colony forming units recovered per ml working solution. Table 4 shows culture densities on the different agars after 48 hours incubation.
Table 5 shows culture densities on Luria Agar with and without Autoinducer after 24 and 48 hours incubation.
Conclusion
There is no difference between recovery of un-injured cells on complex and selective media with and without autoinducer.
There is no difference between recovery of injured cells on complex medium (Luria Agar) with and without inducer after 48 hours, but there is a trend towards quicker growth/recovery (higher number of colonies after 24 hours) on Luria Agar with Autoinducer compared to the same medium without Autoinducer.
There is a significant increase in recovery of injured cells on selective medium (VRGBA) with inducer compared to VRGBA without inducer.
Discussion
The higher recovery of injured organisms on the selective agar with Autoinducer indicates an improvement in tolerance to selective agents (Bile salts and Crystal Violet) and/or improved repair of injured organisms.
The higher number of colonies found after 24 hours on Luria Agar with Autoinducer compared to controls without Autoinducer implies quicker recovery/growth in the presence of Autoinducer.

TABLE 4

| Culture density 48 hrs incubation ($\times 10^3$) | LA | VRGBA | LA + I | VRBGA + I |
|---|---|---|---|---|
| Control | 27 | 28 | 29 | 30 |
| Frozen | 11 | 2.8 | 11 | 5.1 |

Culture densities on 4 different agars after 48 hours at 22° C.

TABLE 5

| Culture density ($\times 10^3$) | LA 24 hrs | LA 48 hrs | LA + I 24 hrs | LA + I 48 hrs |
|---|---|---|---|---|
| Control | 26 | 27 | 29 | 29 |
| Frozen | 6.9 | 11 | 8.5 | 11 |

Culture densities on Luria Agar with and without Autoinducer after 24 and 48 hours incubation at 22° C.

REFERENCES

Eberhard, A. (1972). Inhibition and activation of bacterial luciferase synthesis. J. Bact. 109(3): 1101-5
Eberhard, A., Burlingame, A. L., Kenyon, G. L. Nealson, K. H. & Oppenheimer, N. J. (1981). Structural identification of autoinducer of *Photobacterium fischeri* luciferase. Biochem. 20(9): 2444–2449.
Engebrecht, J. & Silverman, M. (1987). Nucleotide sequence of the regulatory locus controlling expression of bacterial genes for bioluminescence. Nuc. Acids Res. 15(24): 10455–10467.
Engrebrecht, J., Nealson, K. & Silverman, M. (1983). Bacterial bioluminescence: Isolation and genetic analysis of functions from *Vibrio fischeri* Cell 32: 773–781.

Greenberg, E. P., Hastings, J. W. & Ulitzur, S. (1979). Induction of luciferase synthesis in *Beneckea harveyi* by other marine bacteria. *Arch. Microbiol.* 120, 87–91.

Hill, P. J., Swift, S. & Stewart, G. S. A. B. (1991). PCR based gene engineering of the *Vibrio fischeri* lux operon and the *Escherichia coli* trp operon provides for biochemically functional native and fused gene products. *Mol. & Gen. Genet.* in press.

Kaplan, H. B. and Greenberg, E. P. (1987). Overproduction and purification of the luxR gene product: Transcriptional activator of the *Vibrio fischeri* luminescence system. Proc. Natl. Acad. Sci. USA 84: 6639–6643.

Maniatis, T., Fritsch, E. F. and Sambrook, J. (1982). Molecular Cloning; A Laboratory Manual p440. Cold Spring Harbor, N.Y.

Martin, M., Showalter, R. & Silverman, M. (1989). Identification of a locus controlling expression of luminescence genes in *Vibrio harveyi* J. Bact. 171(5): 2406–2414.

Meighen, E. A. (1991). Molecular biology of bacterial bioluminescence. *Microbiol. Rev.* 55, 123–142.

Miyamoto C. M., Meighen, E. A. & Graham, A. F. (1990). Trancriptional regulation of lux genes transferred into *Vibrio harveyi*. J. Bact. 172(4): 2046–2054.

Nealson, K. H., Platt, T. & Hastings, J. W. (1970). Cellular control of the synthesis and activity of the bacterial luminescent system. J. Bact. 104(1): 313–322.

Shadel, G. S., Young, R. & Baldwin, T. O. (1990). Use of regulated cell lysis in a lethal genetic selection in *Escherichia coli*: Identification of the autoinducer-binding region of the luxR protein from *Vibrio fischeri* ATCC7744. J. Bact. 172(7): 3980–3987.

Showalter, R. E., Martin, M. O. & SIlverman, M. R. (1990). Cloning and nucleotide sequence of luxR, a regulatory gene control ling bioluminescence in *Vibrio harveyi* J. Bact. 172(6): 2946–2954.

Silverman, M., Martin, M. & Engebrecht, J. (1989). Regulation of luminescence in marine bacteria. In: *Genetic of Bacterial Diversity* (Hopwood, D. A. & Chater, K. F. eds)., pp 71–86. Academic Press, London.

Slock, J., VanReit, D., Kolibachuk, D. & Greenberg, E. P. (1990). Critical regions of the *Vibrio fischeri* LuxR protein defined by mutational analysis. J. Bact. 172(7): 3974–3979.

Stewart, G. S. A. B, Johnstone, K., Hagelberg, E & Ellar, D. J. (1981). Commitment of bacterial spores to germinate: a measure of the trigger reaction. *Biochem. J.* 198, 101–106.

---

We claim:

1. A method of testing for the presence in a sample of a first bacterium known to generate N-(β-ketocaproyl) homoserine lactone or analogue under particular conditions, which method comprises incubating the sample under the particular conditions in contact with a test bacterium chosen for enhancement of gene expression by the lactone or analogue, and detecting the gene expression as a test for the first bacterium.

2. A method as claimed in claim 1, wherein the first bacterium is selected from *Pseudomonas aeruginosa, Serratia marcescens, Protus mirabilis, Citrobacter freundii* and Enterobacter spp.

3. A method as claimed in claim 1 wherein a fluid sample to be tested for the presence of the first bacterium is filtered, and a nutrient medium containing the test bacterium is laid on the filter and incubated.

4. A method as claimed in claim 1, wherein the gene expression causes bioluminescence.

5. A method as claimed in claim 1, wherein gene expression causes production of antibiotic.

6. A method of controlling autoinducer responsive gene expression in bacteria, except where the gene expression is controlled by a bioluminescent specific luxR gene, which method comprises contacting the bacteria other then *V. fischeri, V. logei* and *V. harveyi*, with a compound having the formula I:

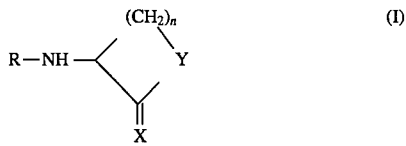

where
n is 2 or 3,
Y is O, S or NH,
X is O, S or NH,
R is $C_1$–$C_{12}$ acyl which may be substituted by a substituent selected from the group consisting of keto, hydroxy, phenyl and alkenyl.

7. A method as claimed in claim 6, wherein, Y is 0, X is 0, n is 2 and R is acyl.

8. A method as claimed in claim 6, wherein R carries a keto or hydroxy group.

9. A method as claimed in claim 8, wherein R carries a keto group in the beta-position.

10. A method as claimed in claim 9, wherein the compound is N-(β-ketocaproyl) homoserine lactone.

11. A method as claimed in claim 6, wherein the gene expression causes bioluminescence.

12. A method as claimed in claim 6, wherein the gene expression causes production of antibiotic.

13. A method as claimed in claim 6, wherein the compound is included in a bacterial growth medium.

14. An optically active isomer of a compound having formula 1 as defined in claim 6.

15. An optically active compound as claimed in claim 14, wherein the isomer is the L-isomer.

16. An optically active compound as claimed in claim 14, wherein the isomer is the D-isomer.

17. A growth medium for bacteria, containing an added compound having formula 1 as defined in claim 6, at a concentration effective to stimulate or promote the metabolism, growth and/or recovery of the bacteria.

18. A growth medium for bacteria containing an added compound having formula 1 as defined in claim 6, at a concentration effective to stimulate or promote the metabolism, growth and/or recovery of the bacteria.

19. A growth medium for bacteria, containing an added compound having formula 1 as defined in claim 6, which compound is an optically active isomer, at a concentration effective to stimulate or promote the metabolism, growth and/or recovery of the bacteria.

20. The growth medium as claimed in claim 19, wherein the optically active isomer is the L-isomer.

21. The growth medium as claimed in claim 19, wherein the optically active isomer is the D-isomer.

* * * * *